(12) United States Patent
Pather et al.

(10) Patent No.: US 6,280,770 B1
(45) Date of Patent: Aug. 28, 2001

(54) MICROEMULSIONS AS SOLID DOSAGE FORMS FOR ORAL ADMINISTRATION

(75) Inventors: S. Indiran Pather, Plymouth; Sangeeta V. Gupte; Rajendra K. Khankari, both of Maple Grove; John Hontz, Plymouth, all of MN (US); Joseph R. Robinson, Madison, WI (US); Jonathan D. Eichman, Ann Arbor, MI (US); Ramya Kumbale, Minneapolis, MN (US)

(73) Assignee: Cima Labs Inc., Eden Prairie, MN (US)

( * ) Notice: Subject to any disclaimer, the term of this patent is extended or adjusted under 35 U.S.C. 154(b) by 0 days.

(21) Appl. No.: 09/374,393

(22) Filed: Aug. 13, 1999

Related U.S. Application Data
(60) Provisional application No. 60/096,347, filed on Aug. 13, 1998.

(51) Int. Cl.[7] .............................. A61K 9/14; A61K 9/20; A61K 9/32; A61K 9/36; A61K 9/46
(52) U.S. Cl. .......................... 424/465; 424/464; 424/478; 424/466; 424/474; 424/489; 424/490; 514/770; 514/937; 514/938
(58) Field of Search ..................................... 424/464, 465, 424/466, 489, 490, 474, 468, 479, 480, 482, 493, 494, 497

(56) References Cited

U.S. PATENT DOCUMENTS

| | | | |
|---|---|---|---|
| 4,353,806 | 10/1982 | Canter et al. | 252/8.55 D |
| 4,360,061 | 11/1982 | Canter et al. | 166/274 |
| 4,751,241 | 6/1988 | Motoyama et al. | 514/532 |
| 5,178,878 | 1/1993 | Wehling et al. | 424/466 |
| 5,206,219 | 4/1993 | Desai | 514/3 |
| 5,393,527 | 2/1995 | Malick et al. | 435/7.1 |
| 5,435,936 | 7/1995 | Broze | 252/162 |
| 5,444,041 | 8/1995 | Owen et al. | 514/2 |
| 5,580,735 | 12/1996 | Malick et al. | 435/6 |
| 5,593,843 | 1/1997 | Malick et al. | 435/7.1 |
| 5,620,903 | 4/1997 | Malick et al. | 436/533 |
| 5,633,226 | 5/1997 | Owen et al. | 514/2 |
| 5,635,357 | 6/1997 | Malick et al. | 435/7.1 |
| 5,646,109 | 7/1997 | Owen et al. | 514/2 |
| 5,688,697 | 11/1997 | Malick et al. | 436/518 |
| 5,688,761 | 11/1997 | Owen et al. | 514/2 |
| 5,800,834 | 9/1998 | Spireas et al. | 424/451 |

OTHER PUBLICATIONS

Microemulsion technology in the reformulation of cyclosporine: the reason behind the pharmacokinetic properties of Neoral, Ritschel, Clin. Transp. 1996: 10: 364–73.

A comparison of two quality assessment methods for emulsions, Pather et al., J. Pharm. &Biomedical Analysis, 1995: 13: 1283–89.

Spieras, et al., "Powdered Solution Technology: Principles and Mechanisms", J. Pharm. Res., 9(10):1351–58 (1992).

Sheth, A. and Jarowski, C.I., "Use of Powdered Solutions To Improve The Dissolution Rate of Polythiazide Tablets", Drug Dev. Ind. Pharm., 16(5):769–77 (1990).

Jonathan D. Eichman, "Mechanastic Studies On Effervescent–Induced Permeability Enhancement" Dissertation, University of Wisconsin–Madison (1997).

(List continued on next page.)

Primary Examiner—James M. Spear
(74) Attorney, Agent, or Firm—Lerner, David, Littenberg, Krumholz & Mentlik, LLP (57) ABSTRACT

Novel pharmaceutical compositions which improve the rate and/or extent of absorption of drugs are disclosed. The novel pharmaceutical compositions of the present invention comprise drug-containing microemulsions adsorbed onto solid particles which may be further formulated into solid dosage forms. The compositions and dosage forms of the present invention improve the bioavailability of a wide range of drugs including drugs that are known or suspected of having poor bioavailability by the utilization of several different mechanisms.

26 Claims, 2 Drawing Sheets

FIGURE 1: TABLET TO BE SWALLOWED

OTHER PUBLICATIONS

Guillemet, F. and Piculell, L., "Interactions in Aqueous Mixtures of Hydrophobically Modified Polyelectrolyte and Oppositely Charged Surfactant. Mixed Micelle Formation and Associative Phase Separation", J. Phys. Chem., 99:9201–09 (1995).

Nelson, Ph.D., E., "Part VXII. Physicochemical and Pharmaceutic Properties of Drugs that Influence the Results of Clinical Trials", Clin. Pharmacol. Ther., 3(5):673–81 (1962).

Ebert, W. R., "Soft Elastic Gelatin Capsules: A Unique Dosage Form", Pharm. Tech., 1(5):44–50 (1977).

FIGURE 1: TABLET TO BE SWALLOWED

FIGURE 2: SOFT TABLET PREPARED ACCORDING TO THE ORASOLVE TECHNIQUE

MICROEMULSIONS AS SOLID DOSAGE FORMS FOR ORAL ADMINISTRATION

CROSS-REFERENCE TO RELATED APPLICATIONS

The present application claims the benefit of U.S. Provisional Patent Application No. 60/096,347, filed on Aug. 13, 1998, the disclosure of which is hereby incorporated by reference herein.

FIELD OF THE INVENTION

The present invention relates to the field of oral pharmaceutical compositions which have a convenient, patient acceptable formulation and good bioavailability. In particular, the oral pharmaceutical compositions of the present invention include solid, oral dosage forms that incorporate drug-containing microemulsions.

BACKGROUND OF THE INVENTION

The difficulty of bringing pharmaceutical substances with problematic bioavailability into a satisfactory pharmaceutically administerable form is generally known. With several drugs, absorption may be as little as 30%, or less, of the orally administered dose when administered in a conventional dosage form, i.e., when no special mechanism is used to enhance absorption of the drug. In addition, poorly adsorbed drugs often display large inter- and intra-subject variability in bioavailability. See Aungst, B. J., J. Pharm. Sci., 82:979–987, 1993. Specific examples (with the average bioavailability given in parentheses) include methyldopa (25%) with a range of 8% to 62%; and nalbuphine (approximately 17%) with a range of 6% to 40%.

The absorption of most drugs depends on two processes: (1) the dissolution of the drug in physiological fluids and (2) the absorption process itself, i.e., the process by which a drug in solution enters the cells at the absorption site and, finally enters general circulation. Many drugs are adsorbed by passive diffusion, i.e., a spontaneous migration of drug molecules from a region of high concentration to a region of low concentration. Other drugs are adsorbed by facilitated or active transport which involve the expenditure of energy by the body. In either event, the dissolution of the drug is the first step in the absorption process unless the drug is administered as a solution. On the other hand, some drugs are adsorbed by the process of pynocytosis or endocytosis which involve the engulfing of solid particles and the incorporation of such particles into the cellular contents.

To compensate for the poor adsorption displayed by many drugs, a pharmaceutical formulation may utilize one or more mechanisms to increase the extent to which the administered drug is adsorbed. While there are a vast number of such techniques, these techniques may be grouped into the following broad categories: (1) enhancement of the rate or extent of dissolution; (2) facilitation of an absorption process that would have occurred naturally; and (3) inducement of an absorption mechanism that would not naturally have occurred or which would have occurred to an insignificant extent. Thus, incorporation of a chemical substance that opens tight junctions in order to increase the rate of absorption of a drug that would normally have been adsorbed slowly through the paracellular route is an example of the second technique. On the other hand, incorporation of a drug within oil droplets for the purpose of involving the lymphatic system in the absorption of the drug (where this would not, otherwise, have occurred) is an example of the third technique.

More recently, powdered solution technology has been proposed as a technique for the delivery of water-insoluble drugs. See Spireas et al., "Powdered Solution Technology: Principles and Mechanisms, Pharm. Research, Vol. 9, No. 10 (1992) and Sheth, A. and Jarowski, C. I., "Use Of Powdered Solutions To Improve The Dissolution Rate Of Polythiazide Tablets," Drug Development and Industrial Pharmacy, 16(5), 769–777 (1990). The concept of powdered solutions involves converting drug solutions or liquid drugs into a dry, nonadherent, free-flowing compressible powder by admixing the liquid drugs or drug solutions with a selected carrier. Although the drug is in a solid form, it is held in a solubilized liquid state, which increases the wetting properties of the drug, and therefore enhances the dissolution. Unfortunately, the application of powder solution technology has been limited because the resulting admixture powder generally has poor and erratic flowability and compressibility properties.

SUMMARY OF THE INVENTION

Novel pharmaceutical compositions which improve the rate and/or extent of absorption of drugs are disclosed. The novel pharmaceutical compositions of the present invention comprise drug-containing microemulsions adsorbed onto solid particles which may be further formulated into solid dosage forms. The compositions and dosage forms in the preferred forms of the present invention improve the bioavailability of a wide range of drugs, including those that are known, or suspected of having poor bioavailability, by the utilization of several different mechanisms.

In one aspect of the invention, the administration of the microemulsions on solid particle adsorbents that preferably have diameters in the nanometer range facilitates the absorption of the drug. Although the present invention is not limited by any means of operation, it is believed that upon disintegration of a tablet or multiparticulate which contains the microemulsion, the adsorbent particles aid in the distribution of the microemulsion droplets through a large volume of the gastrointestinal fluids which prevents the formation of large agglomerates of individual droplets.

In another aspect of the invention, the compositions and dosage forms of the present invention are used to enhance the bioavailability of poorly adsorbed drugs that are oil soluble by administering these drugs as oil-in-water (o/w) microemulsions. The oil soluble drug is distributed as droplets of an oily solution throughout the dose. Oil droplets may be adsorbed together with the incorporated drugs, or the oil droplets may be positioned adjacent to the adsorbing surface. From such oil droplets the drug diffuses into the cell membrane. In addition, due to the fact that there are many such droplets, the surface area of the adsorbing tissues with which the droplets make contact is large, thus facilitating absorption.

In a further aspect of the present invention, the microemulsion compositions of the present invention may be used to promote absorption though the M-cells of Peyer's patches which are involved in the absorption of very small solid particles of the order of 10 micrometers. The individual solid support particles only partially release the microemulsions droplets. Thus, following administration there is free microemulsion droplets as well as a number of microemulsion droplets that remain attached to the solid particles. The small size of microemulsion droplet particles means that they may be adsorbed via this route as well.

In addition, drugs that are subject to metabolic breakdown or degradation in the gastrointestinal tract, such as, for example, peptides, proteins, oilgonucleotides and other substances of biological origin, may be protected within the oil droplets of the microemulsions. The microemulsion component of the present invention makes it difficult for enzymes and other chemical substances to react with such drug molecules when they are encased in oil.

Microemulsions have previously been delivered only in the form of soft or hard gelatin capsules, or as a liquid dispensed directly into the patient's mouth. The microemulsions of the present invention are administered in the form of solid particles which may be further formulated into solid dosage forms. The drug-containing microemulsions are adsorbed onto a solid particulate (i.e., powder). Although the drug is in a solid form, it is maintained as a microemulsion, or in the case of self-microemulsifying drug delivery system ("SMEDDS"), in a state readily converted to a microemulsion in vivo, which thereby enhances the dissolution.

In addition to enhancing the saturation concentration (saturation solubility) of the pharmaceutical substance, the pharmaceutical compositions and solid dosage forms of the present invention also increases the substance surface area of the drug-containing microemulsion. The adsorbent particles increase the area available for interaction with gastrointestinal fluids and/or with the site of absorption to thereby promote absorption of the drug.

The administration of the microemulsions and in a form of a free a solid dosage form also offers significant advantages over the previously available methods of administration. For example, gelatin capsule shells contain water which can migrate into a water-in-oil ("w/o") microemulsions. This can change the proportions of the different phases and/or cause the gelatin shell to become dry and susceptible to cracking. Alternatively, a w/o microemulsion can lose water to the gelatin in which case it swells and becomes soft. Surfactants and co-surfactants within the microemulsions can also react with the capsule shell. On the other hand, oil-in-water ("o/w") microemulsions cannot be incorporated in such capsules because the water in the external phase will react with the capsule shell.

Capsules containing liquids also present handling problems to both the patient and the manufacturers. Capsules leakage is a common problem and therefore sophisticated detection systems must be employed to monitor leakage. Upon physical handling by the patient, the capsule may also soften or leak. With prolonged storage at temperatures and humidity levels that are not as closely controlled as the environment in a pharmaceutical factory, the capsule may also swell, shrink or leak. Thus the present invention eliminates or reduces these problems.

Another aspect to this invention is the presentation of microemulsions in a dosage form that is convenient, easy to handle as compared to existing presentations. The solid dosage forms present a more robust, stable dosage.

A further aspect of the invention relates to a dosage form that is more patient-acceptable and thus provides potential for better patient compliance. There are many patients who do not like to take capsules and for whom an alternate dosage form, such as a tablet, is preferable. In addition, the present invention provides a form for the oral administration of peptides. Peptides are generally administered by injection, which is unpleasant for the patient.

Another object of this invention relates to an improved method of manufacture of microemulsions compared to the preparation of liquid-filled capsules. The more robust and easy solid dosage forms makes for easier production and packaging.

Yet another aspect of the invention relates to the use of various ingredients and/or techniques in combination with the dosage forms of the present invention to further enhance bioavailability, including, the administration of agents which aid in the site specific delivery of the drug-containing microemulsions, agents which increase the rate of dissolution, such as, for example, effervescent agents and disintegration agents, and agents which increase the absorption at the intended site, including, for example, pH adjusting substances and bioadhesives. The use of surfactants in the present dosage forms can be used to enhance the permeability of water soluble, but poorly adsorbed, drugs that are delivered as w/o microemulsions through the structural and fluidity changes to the biological membranes.

BRIEF DESCRIPTION OF THE DRAWINGS

FIG. 1 is an enlarged top plan view of a tablet with adsorbed drug-containing microemulsion.

FIG. 2 is a schematic for the preparation of a soft tablet consisting of agglomerates of adsorbent containing adsorbed microemulsion which are coated with an enteric material.

DETAILED DESCRIPTION OF THE INVENTION

The pharmaceutical compositions of the present invention comprise pharmaceutical carrier microemulsions which are adsorbed onto solid particulate adsorbents. The term "carrier" microemulsion adsorbents is used herein to refer to the product of absorption. Instead of administering the microemulsion in one of the conventional dosage forms, e.g., as a liquid administered directly into the patient's mouth from a measuring device, or within a soft, or a hard, gelatin capsule, the carrier microemulsions adsorbents desirably are administered as a solid, oral dosage form, such as a tablet, granules, pellets or other multiparticulates, capsules that can contain the drug in the form of minitablets, beads, or a powder.

The microemulsion solid particles and/or dosage forms are prepared by adsorbing the microemulsion onto a articulate solid material so as to provide the adsorbent in the form of a powder. The powder can then be made into other solid dosage forms by combination with additional excipients, using appropriate processing.

A microemulsion is an optically isotropic and thermodynamically or kinetically stable system. Microemulsions are composed of an oil phase, an aqueous phase, a surfactant and sometimes a co-surfactant. Microemulsions differ from (macro or coarse) emulsions in that the dispersed phase consists of globules less than 100 nanometers (nm) (0.1 micrometers) and more particularly about 30 to about 60 nm in diameter. The differences between coarse emulsions and microemulsions, however, is not only one of size of the dispersed phase. Microemulsions do not separate on standing, whereas emulsions will separate, even though this may only occur after several years. Microemulsions are transparent because the small droplets of the internal phase do not refract light.

Microemulsions also form easily, sometimes spontaneously, when the components are combined in the correct proportions. In other instances, light mixing with simple apparatus such as a propeller mixer is sufficient to form the microemulsion. Unless ingredients which are solid at room temperature are used, there is no need for the use of heat in the preparation of microemulsions. This is different from coarse emulsions which normally require specialized equipment, such as turbine mixers and homogenizers for the preparation of the liquids that normally have to be heated. Scale up from research and development lots to production batches is also easy. Microemulsion also have a long shelf life, a low viscosity for easy transport and mixing, and, being translucent, are easy to monitor spectroscopically. Thus, the preparation of microemulsions, particularly on an industrial scale, is simplified (compared to emulsions).

The microemulsions of the present invention include oil-in-water (o/w) microemulsions, in which the oil is in the internal phase; water-in-oil (w/o) microemulsions, in which the water is in the internal phase; and bicontinuous microemulsions, in which the entire microemulsion cannot be clearly designated as either w/o or o/w but localized areas have the properties of either type. The present invention also includes the use of self-microemulsifying drug delivery system (SMEDDS). SMEDDS consists of all the components of a microemulsion (oil, surfactant, co-surfactant, antioxidant, preservative) except they do not contain water. However, upon administration of the SMEDDS and admixing with the gastrointestinal fluids, the SMEDDS forms a microemulsion in vivo.

Drug containing water-in-oil microemulsions are made by dissolving a drug in a hydrophilic phase, and then mixing the solution with an oil, and eventually with an aqueous phase. Drug containing oil-in-water microemulsion similarly by admixing the various components. An acceptable SMEDDS may be prepared in accordance with the disclosure set forth in Owen et al., U.S. Pat. No. 5,444,041, which is hereby incorporated by reference herein.

For the manufacture of microemulsions, any industrial mixer of a suitable size may be used. It is not necessary to use a high shear mixer and a conventional propeller mixer may suffice. It is also not necessary to heat the various components of the microemulsion.

Any nontoxic oil may be used in the microemulsions. These include mono-, di- and triglycerides, fatty acids and their esters and esters of propylene glycol or other polyols. The fatty acids and esters used as such or where they form part of a glyceride may be short chain, medium chain or long chain. The ingredients may be of vegetable or animal origin, synthetic or semisynthetic. The oils include, but are not limited to natural oils, such as cottonseed oil, soybean oil, sunflower oil; canola oil; Captex® (various grades); Miglyol®; and Myvacet®.

Any nontoxic surfactant may also be used in the microemulsion, including, but not limited to, various grades of the following commercial products: Arlacel®; Tween®; Capmul®; Centrophase®; Cremophor®; Labrafac®; Labrafil®; Labrasol®; Myverol®; and Tagat®.

It is often unnecessary to include a co-surfactant in the microemulsion, when the microemulsion is formulated with the appropriate choice of low-HLB and high-HLB surfactants. However, where a co-surfactant is required, the co-surfactant is preferably selected from any non-toxic short and medium chain alcohols, but is not limited to these.

The liquid microemulsion can be adsorbed onto the solid particulate adsorbent by the use of a planetary mixer, a Z-blade mixer, a rotorgranulator or similar equipment. Preferably, the amount of microemulsion is kept sufficiently low so that the mixture of adsorbent and microemulsion forms an easily compressible, free-flowing powder. The proportion of microemulsion to solid support preferably varies from about 1:20 to about 10:1. More preferably, the proportion of microemulsion to solid support is about 1:2 to about 2:1.

Any suitable nontoxic adsorbent may be used in accordance with the present invention. Preferably, fine particulate adsorbents are used. Suitable adsorbents for the preparation of products described in this disclosure include, but are not limited to, clays such as kaolin, bentonite, hectorite and Veegum®; silicon dioxide (Cab-O-Sil® or Aerosil®); magnesium trisilicate; aluminum hydroxide; magnesium hydroxide, magnesium oxide or talc. More preferably the adsorbent is silicon dioxide.

The resulting product should preferably be a free-flowing, compressible powder. Once the microemulsion is adsorbed onto the solid support, ideally, the powder should resemble a completely dry powder (as far as observation with the eye can discern) and the powder should also be free-flowing. This is more easily achieved with a o/w microemulsion, partly due to the fact that the water in the external phase partially evaporates during the incorporation process. There is an equilibrium amount of water that is retained on the particles of the solid support. When adsorbing a w/o microemulsion, there is a greater tendency for the powder to appear slightly "damp". Nevertheless, even with a w/o microemulsion the powder should be cohesive. Obviously, the proportions of microemulsion to solid support will determine the extent to which the powder remains free-flowing and dry. However, With the proportions of solid support to microemulsion referred to earlier, it is possible to obtain a noncohesive mixture. This mixture is then mixed with the other tableting components to obtain a compressible mix. It is essential that this compressible mix be free-flowing. This is determined by the angle of repose test as detailed in any standard pharmaceutical text such as "The Theory And Practice Of Industrial Pharmacy" by Lachman, Lieberman and Kanig (Lea and Febiger, publishers), hereby incorporated by reference herein. The static angle of repose test is preferred. When such a test is performed, the final powder blend should have preferably an angle of repose less than 42 degrees, and preferably less than 40 degrees.

Any active substance may be used in the microemulsion carrier. Both liquid drugs and drug solutions are suitable for use in the present invention. In addition the present invention is applicable to both water-soluble and water-insoluble drugs. If water-insoluble drugs are used, the drugs may be dissolved in any nontoxic solvent, including, for example, edible oils.

The pharmaceutical compositions and dosage forms of the present invention are particularly suitable for the oral administration of active substances that display poor bioavailability, slow absorption or long $t_{max}$. These include drugs that are poorly adsorbed, drugs that are degraded during passage through the gastrointestinal system, such as, for example, proteins, peptides and other substances of biological origin. In particular, the protection offered to a drug contained within the internal oil phase of a microemulsion makes this system particularly suitable for proteins and peptides and other biologicals. The pharmaceutical compositions and dosage forms are also suited for the delivery of small molecule drugs and nutritional supplements, such as vitamins and minerals.

Examples of drugs suitable for incorporation into the described systems include, but are not limited, to: acyclovir; auranofin; bretylium; cytarabine; doxepin; doxorubicin; hydralazine; ketamine; labetalol; mercaptopur; methyldopa; nalbuphine; nalozone; pentoxifyll; pridostigm; terbutaline; verapamil; buserelin; calcitonin; cyclosporin; and oxytocin.

The microemulsions may be administered in the form of a tablet, granules, pellets or other multiparticulates, capsules that can contain the drug in the form of minitablets, beads, and as a powder, or any other suitable dosage form.

The dosage forms preferably contain materials that aid in releasing the drug in a specific section of the gastrointestinal tract, thus promoting site-specific delivery. The chosen site for drug release is usually the most efficiently adsorbing part of the gastrointestinal tract for the drug in question, or one that is selected because it offers some other therapeutic advantage. There are various mechanisms by which such materials promote site-specific delivery and this invention is not limited to any one mechanism. For example, the material may be metabolized by enzymes present in a specific part of the gastrointestinal tract, thus releasing the drug in that section. The materials used to promote site-specific absorption may be used as coatings and/or matrix materials to aid in site specific delivery, include, for example, sugars, polysaccharides, starches, polymers, and the like.

If a coating is used, it may be applied to the entire dosage form or to the individual particles of which it consists. The coating can also be used in conjunction with an effervescence to cause the effervescence to occur at specific areas of the gastrointestinal tract. Nonlimiting examples or coatings used in the present invention include: cellulose derivatives including cellulose acetate phthalate (CAP); shellac and certain materials sold under the trademark Eudragit™ (various grades may be used in specific combinations). Hydroxypropylmethyl cellulose phthallate in a grade that dissolves at pH 5 is the preferred coating material.

Coating may preferably be done in a fluidized bed coater ("fbc") or a coating pan. While either type may be used for both tablets and multiparticulates, the fbc is preferred for multiparticulates while the pan coater is preferred for tablets. In the fbc process, the multiparticulates are first prewarmed within the apparatus by blowing warmed air through the container. If the active is a peptide, low temperatures are used so that the potency of the drug is not affected. The volume of fluidizing air penetrating the bed per hour is chosen such that the material to be coated is fluidized and flowing in a gentle pattern. The effect of the atomizing air should, additionally, be taken into account. The bed of material should neither be stationary not lifted largely towards the filter bags. The coating solution is sprayed on at a rate that will wet the material to be coated within the spray zone, have time to flow around the particulates and then be dried within the drying zone of the apparatus. If the liquid spray rate is too slow (or the temperature of the inlet air is too high, or the inlet air is too rapid), the liquid droplets dry before they touch the particles, resulting in the addition of spray dried material to the multiparticulates. When the spray rate is too slow (or the inlet air is introduced too slowly, or its temperature is too low) the liquid does not dry fast enough. The material remains wet, causing agglomeration of the material. At the correct conditions, the coating material neither dries too quickly or wets the material to be coated for a prolonged time. These conditions can be adequately chosen by one ordinarily skilled in the art.

When tablets are coated, this can preferably be done in a coating pan. Many of the modern, perforated pans have feature which make for more efficient coating. As an example the Hicoater (Vector Corporation, Iowa) may be used. The tablets within the pan are preheated and the pan is rotated at a rate that allows gentle tumbling of the tablets. Many of the comments regarding the actual process (such as rate of wetting of the material) made for the fbc, apply to the pan coater as well. The coating solution should be non-aqueous when effervescent material is incorporated within the preparation.

Precoating materials may also be used in the present invention. Nonlimiting examples of precoating materials include cellulose derivatives such as methylcellulose, hydroxypropyl cellulose, hydroxypropyl methylcellulose or combinations and certain materials sold under the trademark Eudragit™ (various grades which may be combined). Hydroxypropylmethyl cellulose phthallate in a grade that dissolves at pH 5 is the preferred coating material.

Other ingredients or techniques may preferably be used with the present dosage forms to enhance the absorption of the pharmaceutical ingredient, to improve the disintegration profile, and/or to improve the organoleptic properties of the material and the like. The selected enhancement technique is preferably related to the route of drug absorption, i.e., paracellular or transcellular. These techniques include, but are not limited to, the use of additional chemical penetration enhancers; mucoadhesive materials; effervescent couples; ion pairing or complexation; and the use of lipid and/or surfactant drug carriers.

A bioadhesive polymer may be included in the dosage form to increase the contact time between the dosage form and the mucosa of the most efficiently adsorbing section of the gastrointestinal tract. See Jonathan D. Eichman, "Mechanastic Studies On Effervescent-Induced Permeability Enhancement," University of Wisconsin-Madison (1997), hereby incorporated by reference herein. Nonlimiting examples of known bioadhesives used in the present invention include: carbopol (various grades), sodium carboxy methylcellulose, methylcellulose, polycarbophil (Noveon AA-1), hydroxypropyl methylcellulose, hydroxypropyl cellulose, sodium alginate, and sodium hyaluronate.

Disintegration agents may also be employed to aid in dispersion of the drug in the gastrointestinal tract. Disintegration agents include any pharmaceutically acceptable effervescent agent. In addition to the effervescence-producing disintegration agents, a dosage form according to the present invention may include suitable noneffervescent disintegration agents. Nonlimiting examples of disintegration agents include: microcrystalline cellulose, croscarmelose sodium, crospovidone, starches and modified starches.

Apart from the effervescent material within the tablet, some additional effervescent components or, alternatively, only sodium bicarbonate (or other alkaline substance) may be present in the coating around the dosage form. The purpose of the latter effervescent/alkaline material is to react within the stomach contents and promote faster stomach emptying.

Additionally, pH adjusting substances, as described in U.S. patent application Ser. Nos. 09/302,105 and 09/327,814 now U.S. Pat. No. 6,200,604, hereby incorporated by reference herein, may also be used to increase absorption of a drug.

Figure 1:
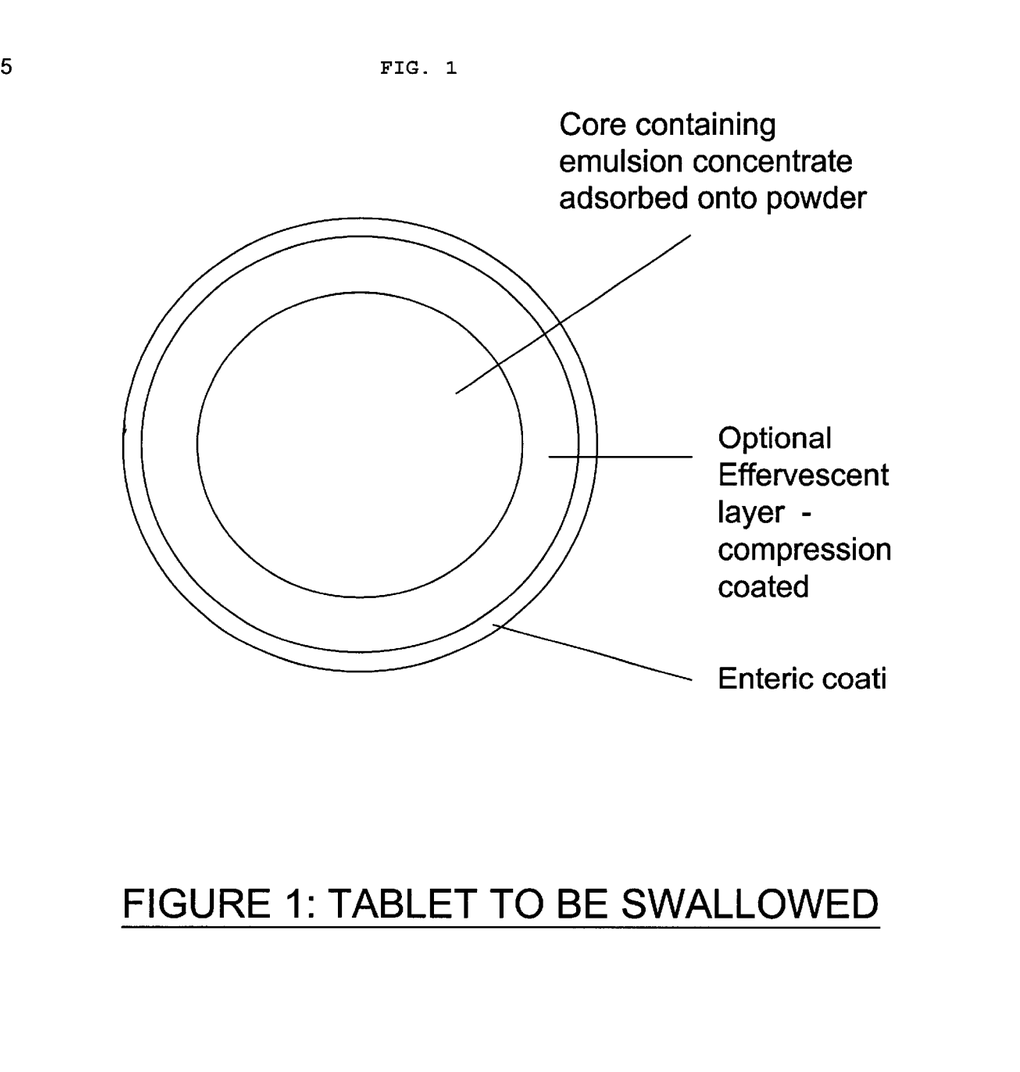

The various components may be present in layers within the dosage form or specialized shapes and geometric arrangements may be employed. FIG. 1 illustrates a tablet made in accordance with the present invention. When the tablet reaches the small intestine, the enteric coat dissolves, exposing the effervescent layer. Reaction of this layer with the aqueous fluid of the gastrointestinal tract releases carbon dioxide. This aids absorption in several ways including, for example, the thinning of the mucus layer, brings the tablet into closer contact with the mucosa. With the dissolution of the effervescent layer, the core of the tablet is exposed, facilitating both the release of the microemulsion droplets from the adsorbent and subsequent drug release from the microemulsion.

Figure 2:
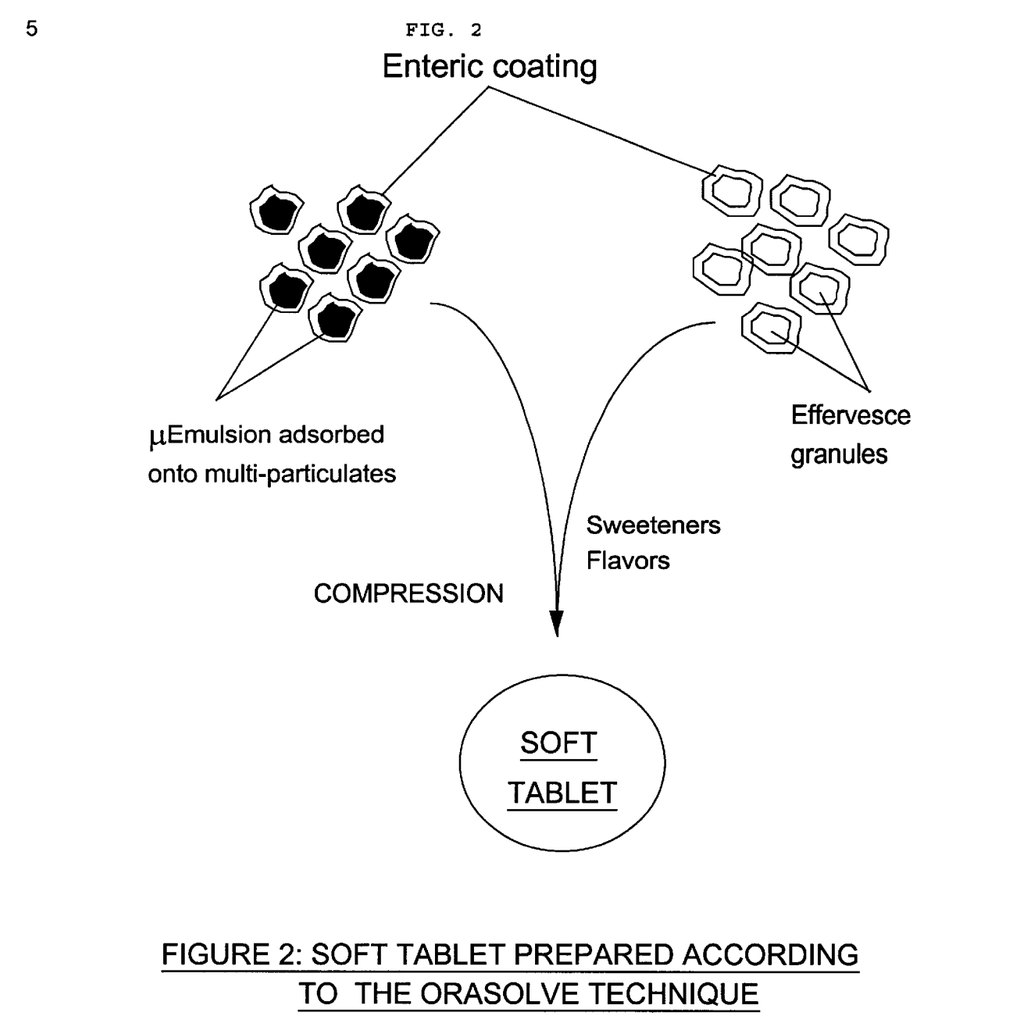

A second design, which is illustrated in FIG. 2, consists of agglomerates of adsorbent (containing adsorbed microemulsion) which are coated with an enteric material. A separate batch of effervescent granules are similarly coated with an enteric material. The two sets of granules are then compressed together into a relatively soft tablet according to the OraSolve® technique, with flavors, sweeteners, disintegrants and other excipients added. Such a tablet, which may be much larger than a conventional tablet, is allowed to disintegrate within the oral cavity. Disintegration, which usually occurs within 2 minutes and more, preferably within 1 minute, releases the enteric-coated granules which are swallowed. This enables absorption to occur at a site distal to the oral cavity. Absorption usually occurs in the duodenum, however, the preparation can contain other components which promote absorption at other sites such as, but not limited to, the colon.

A variation of this design is one in which the material does not contain an enteric coat, nor does it disintegrate rapidly, but is retained in the oral cavity where the drug is released for absorption by the oral mucosa. When the latter design is utilized, the tablet may contain additional penetration enhancers, mucoadhesives or other agents to facilitate absorption in the oral cavity.

Tablets can be manufactured by wet granulation, dry granulation, direct compression or any other tablet manufacturing technique. Soft tablets are preferably made by direct compression in accordance with the disclosures in U.S. Pat. No. 5,178,878, which are hereby incorporated by references herein. For peptides and other substances of biological origin, low compression forces are preferable because these substances are sensitive to compression forces. With such compounds, the conformation of the compound and its biological activity can change with conventional compression forces.

The tablet may be a layered tablet consisting of a layer of the active ingredients set forth above in layers of diverse compositions. In accordance with the present invention, the tablet size is preferably up to about ¾". The tablet hardness is preferably between about 5N and about 50N and more preferably between about 5N and 35N. Excipient fillers can be used in connection with the present invention to facilitate tableting. Nonlimiting examples of fillers include: mannitol, dextrose, lactose, sucrose, and calcium carbonate. For a tablet intended to disintegrate in the oral cavity, the mass of the tablet should, preferably, not exceed 2.5 g. If an effervescent agent is included, the effervescence level in the tablet is preferably between about 5% and 95% by weight based on the weight of the finished tablet.

Pellets or other multiparticulates may be manufactured by granulation, layering techniques, extrusion and spheronization or other pellet manufacturing methods. Multiparticulates are preferably made by dry granulation (including chilsonation). The multiparticulate size is preferably up to about 3 mm. Coating of the dosage forms or the multiparticulates may be accomplished in a fluid bed coater or by other coating techniques. The multiparticulates may be packed into capsules.

Granules may be made by a wet granulation process or a dry granulation process. When wet granulation is used, isopropyl alcohol, ethyl alcohol or other nonaqueous granulating agent is used. Low moisture content grades of these organic solvents are used. Dry granulation may be achieved through slugging or chilsonation. Layering may be done in a fluid bed apparatus or coating pan. Nonaqueous binders are used to aid the adherence of the added material (drug, effervescent penetration enhancer and excipients) to the starting material. Nonlimiting examples of the starting material or cores are nonpareils (sucrose) or microcrystalline cellulose seeds.

The invention will further be described by reference to the following detailed examples. These examples are provided for the purpose of illustration only, and are not intended to be limiting unless otherwise specified.

EXAMPLE 1

Preparation of Oil-in-water Microemulsion

| Ingredients | Amount in g |
| --- | --- |
| Testosterone propionate | 1.5 |
| Miglyol 812 (triglycerides from coconut oil) | 2 |
| Brij 96 (polyoxyethylene 10-oleyl ether) | 17.5 |
| Water qs | 100 |
| Total | 100 |

Procedure: Heat Brij 96 (nonionic surfactant) in waterbath at 90 C. Then, allow to cool and add Miglyol 812 and testosterone propionate to the above. This mixture is vigorously stirred until a homogenous dispersion is obtained. Water is added to this dispersion and stirred until a clear microemulsion is obtained.

EXAMPLE 2

Adsorption of Microemulsion Onto Silicon Dioxide

| Ingredients | Amount in g |
| --- | --- |
| Microemulsion | 25 |
| Colloidal Silicon dioxide | 75 |
| Total | 100 |

Procedure: Take colloidal silicon dioxide in a planetary mixture and add the microemulsion slowly with continuous mixing to obtain a powder.

EXAMPLE 3

Formula for Tablets Using Oil-in-water Microemulsion

| Ingredients | mg/500 mg tablet | % w/w per tablet | g/batch |
| --- | --- | --- | --- |
| Microemulsion adsorbed onto Silicon dioxide (3:1) | 251.5 | 50.3 | 50.30 |
| Prosolv 90 | 153.0 | 30.6 | 30.60 |
| Sodium Bicarbonate | 38.5 | 7.7 | 7.70 |
| Citric Acid | 16.5 | 3.3 | 3.30 |
| Crospovidone | 33.0 | 6.6 | 6.60 |
| Magnesium Stearate | 7.5 | 1.5 | 1.50 |
| Total | 500.0 | 100.0 | 100.00 |

Procedure: Weigh and screen all materials except Magnesium Stearate and blend for 30 minutes in a blender. Then, weigh and screen Magnesium Stearate, add to above blend and mix a further 5 minutes. Discharge blend and compress tablets.

EXAMPLE 4

Coating Solution Formula

| Ingredients | g/batch |
|---|---|
| Hydroxypropylmethylcellulose pthalate (HP 55S) | 372 |
| Triethyl Citrate | 28 |
| Ethanol | 1800 |
| Acetone | 1800 |
| Total | 4000 |

Procedure: The coating solution is prepared by adding HP 55S to ethanol and acetone stirring vigorously in a large beaker. The mixture is allowed to stir until the HP 55S has gone into solution completely. Triethyl Citrate is then added and stirred further to obtain the final solution used to coat tablets.

EXAMPLE 5

Coating

The coating is carried out in a coating pan to avoid friability of the tablets. The airflow during the coating is maintained at 30 CMH (cubic meters/hr) and spray rate is 9.5 g/min. The pan speed is maintained at 20 rpm. The inlet air temperature is maintained between 42 and 45 C. and coating is continued until a weight gain of 15% is obtained.

We claim:

1. A microemulsion composition in the form of a free-flowing, compressible powder, comprising:
   an admixture of a drug-containing microemulsion and a solid particle adsorbent; wherein said microemulsion is adsorbed on said solid particle adsorbent and forms a free-flowing, compressible powder.

2. The microemulsion composition of claim 1, wherein said drug-containing microemulsion is an oil-in-water microemulsion.

3. The microemulsion composition of claim 1 wherein said drug-containing microemulsion is a water-in-oil microemulsion.

4. The microemulsion composition of claim 1, wherein said drug-containing microemulsion is a bicontinuous phase microemulsion.

5. The microemulsion composition of claim 1, wherein said drug-containing microemulsion is a self-microemulsifying drug delivery system which converts to an oil-in-water microemulsion in vivo.

6. The microemulsion composition of claim 1, wherein said solid particle adsorbent is selected from the group consisting of kaolin, bentonite, hectorite, colloidal magnesium-aluminum silicate, silicon dioxide, magnesium trisilicate, aluminum hydroxide, magnesium hydroxide, magnesium oxide and talc.

7. The microemulsion composition of claim 1, wherein the drug-containing microemulsion is a drug that displays poor bioavailability in the gastrointestinal tract of a mammal, when said drug is administered in a form other than said microemulsion.

8. The microemulsion composition of claim 1, wherein the drug in said drug-containing microemulsion includes a drug selected from the group consisting of biological molecules.

9. The microemulsion composition of claim 1, wherein said drug-containing microemulsion includes a drug selected from the group consisting of drugs and nutritional supplements.

10. The microemulsion composition of claim 1, wherein said drug-containing microemulsion includes a drug selected from the group consisting of acyclovir; auranofin; bretylium; cytarabine; doxepin; doxorubicin; hydralazine; ketamine; labetalol; mercaptopur; methyldopa; nalbuphine; nalozone; pentoxifyll; pridostigm; terbutaline; verapamil; buserelin; calcitonin; cyclosporin; and oxytocin.

11. A microemulsion composition in the form of a free-flowing, compressible powder, comprising:
    an admixture of a drug-containing self-microemulsifying drug delivery system and a solid particle adsorbent; wherein said drug-containing self-microemulsifying drug delivery system is adsorbed on said solid particle adsorbent and forms a free-flowing, compressible powder.

12. A solid dosage for the oral administration of a therapeutically effective amount of a drug, comprising:
    an admixture of a drug-containing microemulsion and a solid particle adsorbent; wherein said microemulsion is adsorbed on said solid particle adsorbent and forms a free-flowing, compressible powder.

13. The solid dosage form of claim 12, wherein said solid dosage form is a tablet.

14. The solid dosage form of claim 12, wherein said solid dosage form is a pellet.

15. The solid dosage form of claim 12, wherein said solid dosage form is a multiparticulate.

16. The solid dosage form of claim 12, wherein said solid dosage form is a minitablet.

17. The solid dosage form of claim 12, wherein said solid dosage form further comprises a bioadhesive.

18. The solid dosage form of claim 12, wherein said solid dosage form further comprises an enteric coating maintained over said dosage form; wherein said enteric coating prevents the release of said drug-containing microemulsion until a time at which said dosage form reaches a target area following oral administration.

19. The solid dosage form of claim 12, wherein said solid dosage form further comprises at least one effervescent agent.

20. The solid dosage form of claim 12, further comprising at least one disintegration agent; wherein said disintegration agent causes rapid dispersion of said drug-containing microemulsion to a target area following oral administration.

21. The solid dosage form of claim 12, further comprising a Ph adjusting substance.

22. A method for preparing a microemulsion, comprising the steps of:
    preparing a drug-containing microemulsion;
    converting said drug-containing microemulsion into a free-flowing, compressible powder by admixing said drug-containing microemulsion with a solid particle adsorbent.

23. A method for preparing a solid dosage for the oral administration of a therapeutically effective amount of a drug, comprising the steps of:
    preparing a drug-containing microemulsion;
    converting said drug-containing microemulsion into a free flowing compressible powder by admixing said drug-containing microemulsion with a solid particle adsorbent;
    compressing said free-flowing, compressible powder into a solid dosage form.

24. A stable microemulsion composition which is the product of the process of:

preparing a drug-containing microemulsion;

converting said drug-containing microemulsion into a free-flowing, compressible powder by admixing said drug-containing microemulsion with a solid particulate adsorbent.

25. A method for delivering a drug to a mammal comprising the steps of:

preparing a drug-containing microemulsion;

converting said drug-containing microemulsion into a free-flowing, compressible powder by admixing said drug-containing microemulsion with a solid particle adsorbent;

orally administering said free, flowing compressible powder to a mammal.

26. The microemulsion composition of claim 8, wherein the biological molecules comprise peptides, proteins and oligonucleotides.

* * * * *

UNITED STATES PATENT AND TRADEMARK OFFICE
CERTIFICATE OF CORRECTION

PATENT NO. : 6,280,770 B1
DATED : August 28, 2001
INVENTOR(S) : S. I. Pather, Sangeeta V. Gupte, Rajendra K. Khankari, John Hontz and Ramya Kumbale It is certified that error appears in the above-identified patent and that said Letters Patent is hereby corrected as shown below:

Title page,
Item [75], Inventors: delete "Joseph R. Robinson, Madison, WI (US); Jonathan D. Eichman, Ann Arbor, MI (US);"

Column 1,
Line 28, change "adsorbed" to -- absorbed --.
Line 38, change "adsorbed" to -- absorbed --.
Line 41, change "adsorbed" to -- absorbed --.
Line 42, change "involve" to -- involves --.
Line 46, change "adsorbed" to -- absorbed --.
Line 47, change "involve" to -- involves --.
Line 49, change "adsorption" to -- absorption --.
Line 52, change "adsorbed" to -- absorbed --.
Line 52, change "are" to -- is --.
Line 61, change "adsorbed" to -- absorbed --.

Column 2,
Line 44, change "adsorbed" to -- absorbed --.
Line 48, change "adsorbed" to -- absorbed --.
Line 49, change "adsorbing" to -- absorbing --.
Line 52, change "adsorbing" to -- absorbing --.
Line 61, change "is" to -- are --.
Line 65, change "adsorbed" to -- absorbed --.

Column 3,
Line 1, change "oilgonucleotides" to -- oligonucleotides --.
Line 21, change "increases" to -- increase --.
Line 27, change "a solid" to -- solid --.
Line 30, delete "a"

Column 4,
Line 12, change "adsorbed" to -- absorbed --
Line 30, change "absorption" to -- adsorption --.
Lines 40 and 41, change "articulate" to -- particulate --.

Column 5,
Line 3, change "Microemulsion" to -- Microemulsions --.
Line 24, delete "similarly" and insert -- can be made --.

UNITED STATES PATENT AND TRADEMARK OFFICE
CERTIFICATE OF CORRECTION

PATENT NO. : 6,280,770 B1
DATED : August 28, 2001
INVENTOR(S) : S. I. Pather, Sangeeta V. Gupte, Rajendra K. Khankari, John Hontz and Ramya Kumbale It is certified that error appears in the above-identified patent and that said Letters Patent is hereby corrected as shown below:

Column 6,
Line 13, change "a" to -- an --.
Line 23, change "With" to -- with --.
Line 61, change "mercaptopur" with -- mercaptopurine --.
Line 62, change "pentoxifyll" to -- pentoxifylline --.
Line 62, change "pridostigm" to -- pyridostigmine --.

Column 7,
Line 4, change "adsorbing" to -- absorbing --.
Line 57, change "feature" to -- features --.

Column 8,
Line 19, change "adsorbing" to -- absorbing --.

Column 9,
Line 5, change "OraSolve" to -- OraSolv --.

Column 10,
Line 31, change "Adsorption" to -- Absorption --.
Line 45, before "Example 3", insert -- Tablet Size: ½" Tablet Wt.: 500 mg --.

Column 11,
Line 9, in Example 4, change "pthalate" to -- phthalate --.

Column 12,
Line 6, change "pridostigm" to -- pyridostigmine --.
Line 48, change "Ph" to -- pH --.

UNITED STATES PATENT AND TRADEMARK OFFICE
CERTIFICATE OF CORRECTION

PATENT NO.    : 6,280,770 B1
DATED         : August 28, 2001
INVENTOR(S)   : S. I. Pather, Sangeeta V. Gupte, Rajendra K. Khankari, John Hontz and
                Ramya Kumbale It is certified that error appears in the above-identified patent and that said Letters Patent is hereby corrected as shown below:

<u>Column 14,</u>
Line 5, after "orally administering said" change "free, flowing" to -- free-flowing, --

Signed and Sealed this

Second Day of July, 2002

*Attest:*

*Attesting Officer*

JAMES E. ROGAN
*Director of the United States Patent and Trademark Office*